(12) United States Patent
Shimohira

(10) Patent No.: US 10,058,303 B2
(45) Date of Patent: Aug. 28, 2018

(54) MOBILE X-RAY IMAGING APPARATUS

(71) Applicant: Hitachi, Ltd., Tokyo (JP)

(72) Inventor: Takashi Shimohira, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 153 days.

(21) Appl. No.: 15/301,385

(22) PCT Filed: Mar. 17, 2015

(86) PCT No.: PCT/JP2015/057801
§ 371 (c)(1),
(2) Date: Oct. 1, 2016

(87) PCT Pub. No.: WO2015/151783
PCT Pub. Date: Oct. 8, 2015

(65) Prior Publication Data
US 2017/0020479 A1  Jan. 26, 2017

(30) Foreign Application Priority Data
Apr. 3, 2014  (JP) ................................. 2014-077300

(51) Int. Cl.
*A61B 6/00* (2006.01)
*A61B 6/06* (2006.01)
*A61B 6/10* (2006.01)

(52) U.S. Cl.
CPC .................. *A61B 6/56* (2013.01); *A61B 6/06* (2013.01); *A61B 6/4405* (2013.01); *A61B 6/4429* (2013.01); *A61B 6/10* (2013.01)

(58) Field of Classification Search
CPC .................................................. A61B 6/4405
See application file for complete search history.

(56) References Cited

U.S. PATENT DOCUMENTS 7,635,221 B2    12/2009 Spahn
9,105,441 B2 *  8/2015 Matsuda ................. H01J 35/16
2009/0180595 A1 7/2009 Spahn

FOREIGN PATENT DOCUMENTS

CN    102834054 A    12/2012
CN    102858248 A    1/2013
(Continued)

OTHER PUBLICATIONS

International Search Report dated Apr. 14, 2015 for International Patent Application No. PCT/JP2015/057801.
(Continued)

*Primary Examiner* — Dani Fox

(57) ABSTRACT

In order to provide a mobile X-ray imaging apparatus having less possibility that a cable comes into contact with an object, the apparatus has a carriage and an X-ray imaging unit mounted on the carriage, and the X-ray imaging unit is provided with an X-ray generator, an arm holding one end of the X-ray generator, a supporting post supporting the other end of the arm in a vertically movable manner, and a main body supplying electric power. Conductor filaments are arranged at intervals along an axial direction on the supporting post, conductor brushes coming into contact with the filaments respectively are arranged on the other end of the arm, the brushes move vertically along the filaments in a state of coming into contact with the filaments with the vertical movement of the arm, and the main body supplies electric power to the X-ray generator through the filaments and the brushes.

11 Claims, 9 Drawing Sheets

(56) References Cited

FOREIGN PATENT DOCUMENTS

| | | |
|---|---|---|
| JP | 10174684 A | 6/1998 |
| JP | H10174684 A | 6/1998 |
| JP | 2005224980 | 8/2005 |
| JP | 2008535628 A | 9/2008 |
| JP | 2013523398 A | 6/2013 |
| JP | 201483108 A | 5/2014 |

OTHER PUBLICATIONS

Office Action for the Chinese Application 201580010036.0, dated Jun. 26, 2018, 5 pages.

\* cited by examiner

MOBILE X-RAY IMAGING APPARATUS

CROSS-REFERENCE TO RELATED APPLICATIONS

This application is a national phase claiming the benefit of and priority to International Patent Application No. PCT/JP2015/057801, entitled "MOBILE X-RAY IMAGING APPARATUS", filed Mar. 17, 2015, which claims priority to Japanese Patent Application No. 2014-077300, entitled "MOBILE X-RAY IMAGING APPARATUS", filed Apr. 3, 2014, which are hereby incorporated by reference in their entireties.

TECHNICAL FIELD

The present invention relates to a mobile X-ray imaging apparatus that can be moved to a sickroom and the like to perform X-ray imaging on an object.

BACKGROUND ART

A mobile X-ray imaging apparatus for hospital rounds is used when X-ray imaging is performed on an object in a sickroom or a surgical operating room. The mobile X-ray imaging apparatus has a structure in which an X-ray imaging apparatus is mounted on a mobile carriage, and can be moved to the vicinity of the object's bed by the mobile carriage, which can perform X-ray imaging for the object on the bed.

For example, as shown in Patent Literature 1, a mobile X-ray imaging apparatus has a configuration in which an arm to hold an X-ray tube, a supporting post supporting the arm in a vertically movable manner, and a control device are mounted on a traveling body (carriage). The X-ray tube is connected via the control device and a cable to receive electric power supply.

CITATION LIST

Patent Literature

PTL 1: Japanese Unexamined Patent Publication No. 10-174684
PTL 2: Japanese Unexamined Patent Publication No. 2004-33415

SUMMARY OF INVENTION

Technical Problem

In a mobile X-ray imaging apparatus, cables connecting the X-ray tube and the control device is structurally pulled out around the outside of a supporting post and an arm and reaches the X-ray tube as disclosed in PTL 1. The cable length is set to a length at which the X-ray tube and the control device can be connected in a state where the arm is lifted up to the highest position of the supporting post and is extended maximally.

10 or more cables including not only power source cables supplying a tube current and a tube voltage but also cables supplying electric power for anode rotation, cables for detection signals of the tube current and the tube voltage, and cables for operating electric power of a collimator are generally required.

In a case where an object is imaged by a mobile X-ray imaging apparatus in a sickroom or a surgical operating room, an operator performs positioning operation for imaging that moves the X-ray tube to the vicinity of an imaging site by moving an arm vertically to a supporting post, rotating the supporting post, and extending/contracting the arm. Because a cable is set to a length at which the arm is in the highest position of the supporting post and can reach the X-ray tube in the most extended state at this time, the cable can accidentally come into contact with the object in a state where the arm is lowered halfway on the supporting post or is contracted. However, because a problem occurs in infection prevention if the cable comes into contact with the object, the operator performs the positioning operation by paying meticulous attention so as to prevent the cable from coming into contact with the object. Therefore, it is desirable to use a mobile X-ray imaging apparatus having less possibility of coming into contact with the object with the cable.

The purpose of the present invention is to provide a mobile X-ray imaging apparatus having less possibility of coming into contact with an object with a cable in case of positioning operation for imaging.

Solution to Problem

In order to solve the above problem, the present invention provides the following X-ray imaging apparatus. That is, the X-ray imaging apparatus of the present invention has a carriage and an X-ray imaging unit mounted on the carriage, and the X-ray imaging unit is provided with an arm holding one end of an X-ray generator, a supporting post supporting the other end of the arm in a vertically movable manner, and a main body supplying electric power at least to generate an X-ray to the X-ray generator. A plurality of conductor filaments are arranged at intervals along an axial direction on the supporting post. A plurality of conductor brushes coming into contact with the filaments respectively are arranged on the other end of the arm. The brushes move vertically along the filaments in a state of coming into contact with the filaments with the vertical movement of the arm. The main body supplies electric power to the X-ray generator through the filaments and the brushes.

Advantageous Effects of Invention

According to the present invention, the operability in positioning for imaging of a mobile X-ray imaging apparatus can be improved.

DESCRIPTION OF EMBODIMENTS

Figure 1:
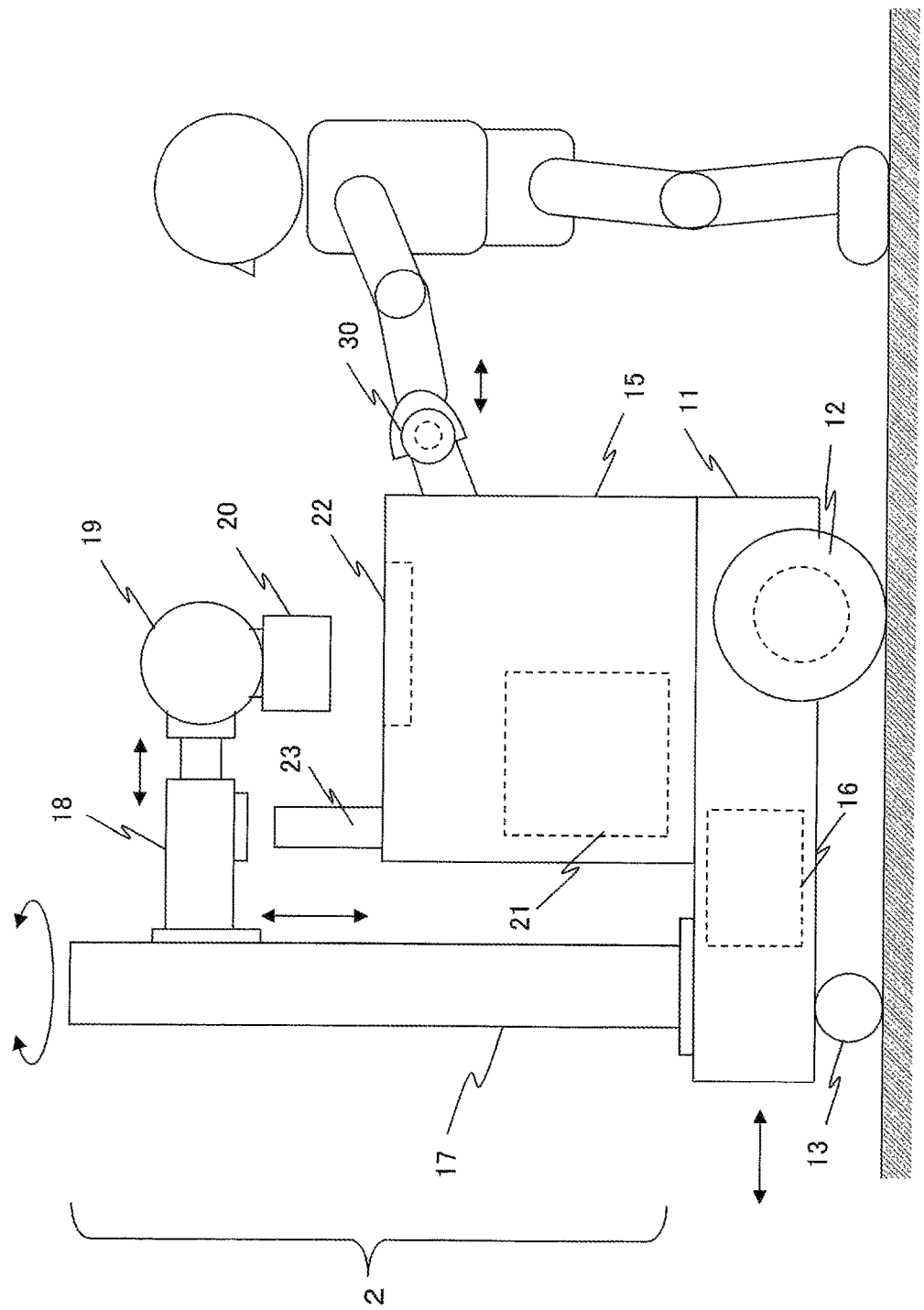
FIG. 1 is a block diagram that schematically shows an overall configuration of a mobile X-ray imaging apparatus of an embodiment.

A mobile X-ray imaging apparatus relating to the present invention has a carriage and an X-ray imaging unit mounted on the carriage, the X-ray imaging unit is provided with an X-ray generator; an arm holding one end of the X-ray generator; a supporting post supporting the other end of the arm in a vertically movable manner; and a main body supplying electric power at least to generate an X-ray to the X-ray generator, a plurality of conductor filaments are arranged at intervals along the axial direction of the supporting post, a plurality of conductor brushes coming into contact with the filaments respectively are arranged on the other end of the arm, the brushes move vertically along the filaments in a state of keeping contact with the filaments with vertical movement of the arm, and the main body supplies the electric power to the X-ray generator through the filaments and the brushes.

Also, an opening is provided along the axial direction on a side surface of the supporting post, a plurality of the filaments are arranged in a space inside the supporting post, and the other end of the arm is inserted in the opening of the supporting post.

Additionally, a plurality of the filaments and a spring to urge the arm in the vertical direction are disposed in a space inside the supporting post, and the space inside the supporting post is separated into a space in which the filaments are arranged and a space in which the spring is disposed by a partition wall.

Furthermore, a plurality of the filaments and a mechanical part to hold a desired position in the vertical direction of the arm are disposed in the space inside the supporting post, first and second partition walls separating a first space in which the mechanical part is disposed; a second space in which the filaments are arranged; and a third space in which the other end of the arm is inserted are disposed in the supporting post, and a slit to pull out lead wires connected respectively to a plurality of the brushes arranged in the second space to the third space is provided along the axial direction of the supporting post on the second partition wall separating the second and third spaces.

Also, the filaments are fixed to an inner wall of the supporting post.

Additionally, the base of the supporting post is rotatably supported around the axial direction of the supporting post on the carriage, a slip ring is disposed in a contact part between the base of the supporting post and the carriage, the slip ring includes a plurality of conductor rings and a plurality of conductor brushes coming into contact with the rings respectively, a plurality of the rings and one ends of a plurality of the conductor brushes are arranged on the supporting post side to electrically connect to the filaments, and the other ends are arranged on the carriage side to electrically connect to the main body.

Also, a plurality of arm filaments electrically connected to a plurality of the brushes respectively are arranged in the arm, and electric power is supplied to the X-ray generator through the arm filaments.

Also, the arm includes a plurality of tubular members with different thicknesses, has a configuration in which thinner tubular members are inserted in thicker tubular members, and can be extended/contracted by moving the thinner tubular members to the thicker tubular members in the axial direction. The arm filaments are arranged inside the thicker tubular members and thinner tubular members respectively, and brushes for the conductor arm are arranged for each of the arm filaments in areas where the thicker tubular members and thinner tubular members overlap.

Also, the X-ray generator is connected to the tip of the arm rotatably around the axial direction of the arm, a slip ring is disposed in the connecting part between the tip of the arm and the X-ray generator, and the arm filaments are electrically connected to conductor rings composing the slip ring and one ends of conductor brushes.

Also, the main body is provided with a controller that generates a control signal to be transmitted to the X-ray generator, the controller and the X-ray generator comprise a transmitter and a receiver respectively, and the control signal is transmitted from the controller to the X-ray generator by wireless communication between the transmitter and the receiver.

Also, the X-ray generator is provided with a battery that supplies electric power to a collimator that sets an X-ray irradiation range, and the battery is connected to the main body and is recharged through the brushes on the other end of the arm and the filaments inside the supporting post.

Next, the embodiment of the present invention will be described in detail using the figures. In the present invention, as described below, a main body of a mobile X-ray imaging apparatus and an X-ray generator are electrically connected without cables to supply electric power from the main body to the X-ray generator.

Figure 2:
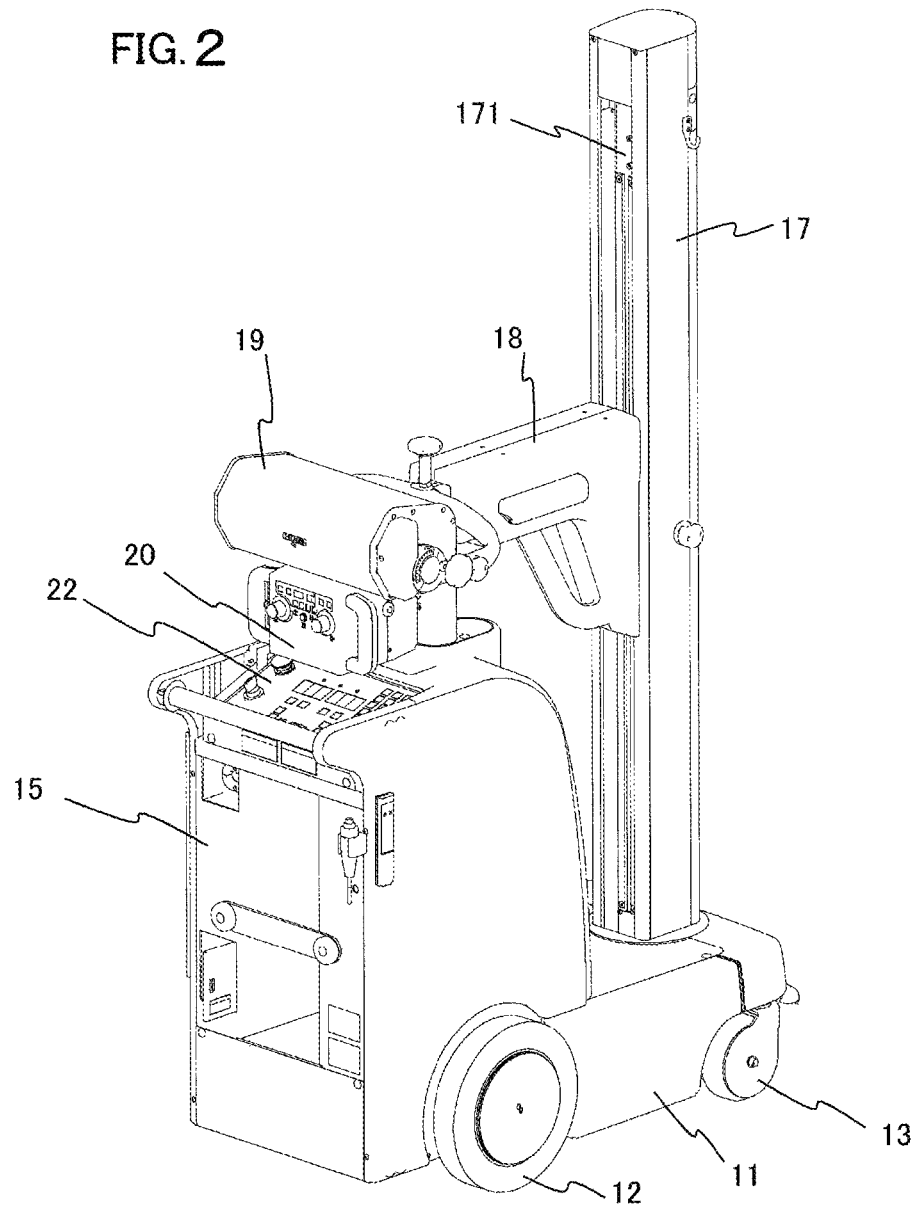
FIG. 2 is a perspective view of the mobile X-ray imaging apparatus of the embodiment.

An overview of the overall configuration and a perspective view of the mobile X-ray imaging apparatus of the present invention are illustrated in FIGS. 1 and 2 respectively. The mobile X-ray imaging apparatus of the present invention includes a carriage 11 and an X-ray imaging unit 2 mounted on the carriage 11.

The X-ray imaging unit 2 includes an X-ray generator 19, an arm 18, a supporting post 17, and a main body 15. The arm 18 holds the X-ray generator 19 at the tip. The other end of the arm 18 is supported in a vertically movable manner by the supporting post 17. The main body 15 supplies electric power at least to generate an X-ray to the X-ray generator 19.

Figure 3:
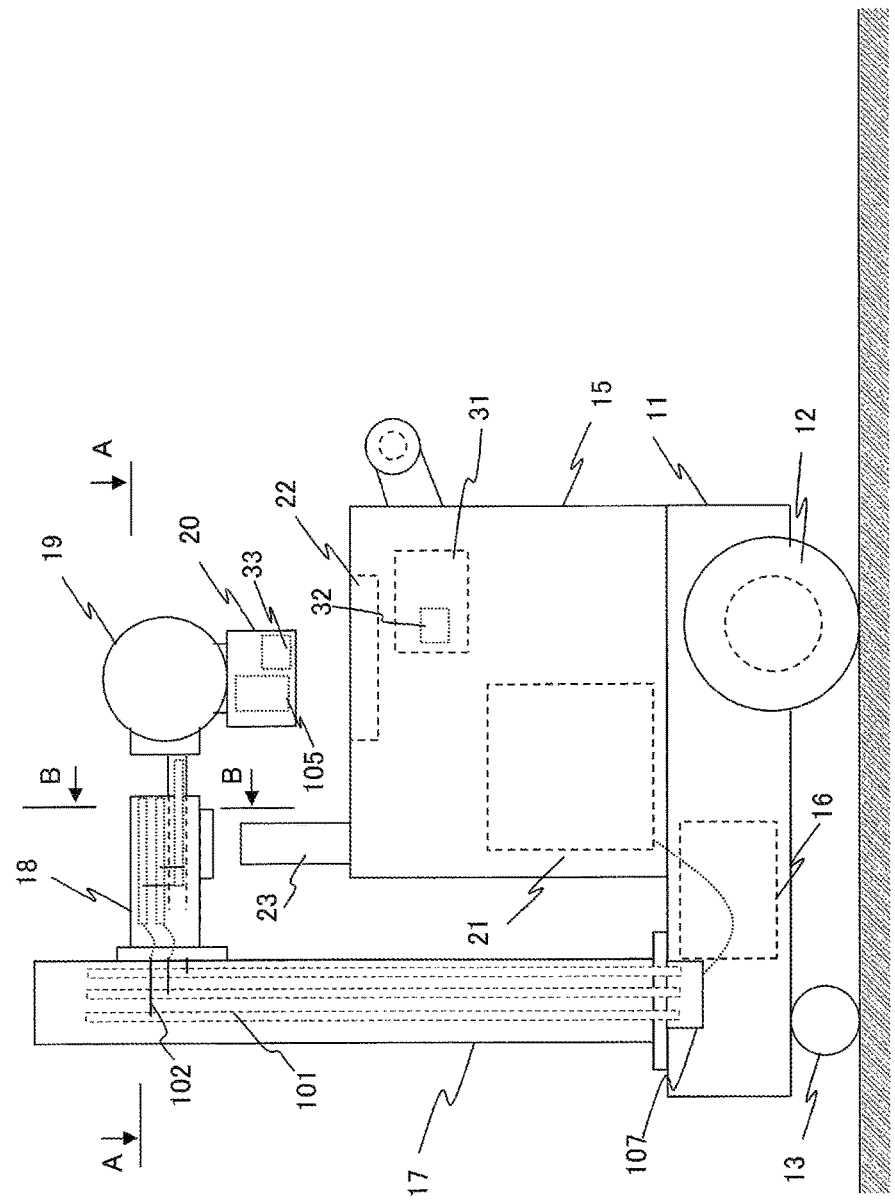
FIG. 3 is a block diagram that shows a configuration of the mobile X-ray imaging apparatus of the embodiment.
Figure 4:
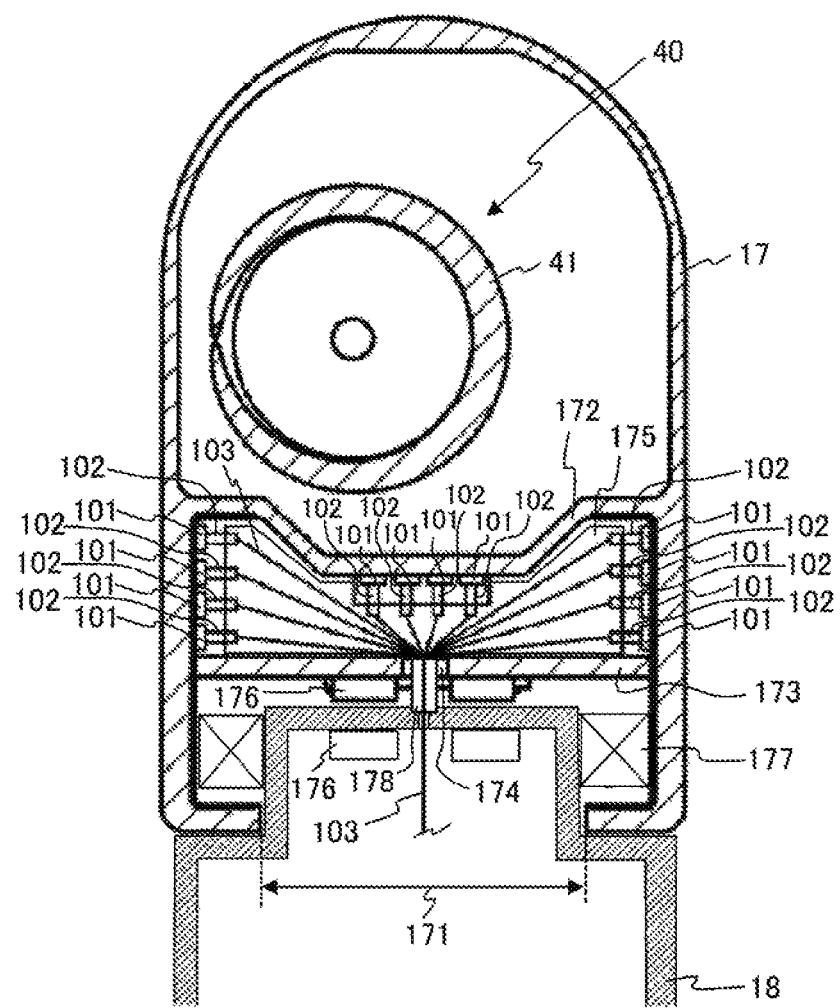
FIG. 4 is an A-A cross-sectional view of a supporting post 17 of FIG. 3.

As a schematic view and a cross-sectional view are illustrated in FIGS. 3 and 4 respectively, a plurality of filaments 101 are arranged at intervals along the axial direction of the supporting post 17. A plurality of brushes 102 coming into contact with the filaments 101 respectively are arranged on the other end of the arm 18 that does not hold the X-ray generator 19. The brushes 102 move vertically along the filaments 101 in a state of keeping contact with the filaments 101 with vertical movement of the arm 18. The main body 15 supplies electric power to the X-ray generator 19 through the filaments 101 and the brushes 102.

Thus, in the present invention, the electric power from the main body 15 can be supplied to the X-ray generator 19 through the supporting post 17 and the arm 18 by the filaments 101 and the brushes 102, which does not need to pull out a power supply cable around the outside of the supporting post 17 and the arm 18.

Additionally, the filaments 101 may be arranged on an inner wall or an outer peripheral surface of the supporting post 17. In a case of arranging on the inner wall of the supporting post 17, a possibility that an operator accidentally comes into contact with the filaments 101 is small, which can safely arrange the filaments 101 supplying large electric power. In a case of arranging on the outer peripheral surface of the supporting post 17, it is desirable to dispose an insulating cover or the like on the outer periphery of the supporting post 17 in order to prevent the operator from coming into contact with the filaments 101.

In a case of arranging the filaments 101 on the inner wall of the supporting post 17, it can be configured to arrange a plurality of the filaments 101 in a space inside the supporting post 17 by providing the opening 171 along the axial direction on a side surface of the supporting post 17 as shown in FIG. 2. In this case, it is configured so as to insert an end of the arm 18, at which the brushes 102 are provided, in the opening 171 of the supporting post 17.

In addition to a plurality of the filaments 101, a mechanical part 40 that allows to manually move a position in the vertical direction of the arm 18 and holds a moved position is disposed in a space inside the supporting post 17 as illustrated in FIG. 4. It is desirable that a partition wall 172 separates a space where the filaments 101 are arranged and a space where the mechanical part 40 is disposed in the space inside the supporting post 17. Hence, there is no possibility that the mechanical part 40 and a plurality of the filaments 101 in which large electric power flows interfere with each other. A widely-known structure can be used for the configuration of the mechanical part 40. For example, the structure disclosed in Patent Literature 2 can be used.

Furthermore, as shown in FIG. 4, a partition wall 173 that separates the space where the filaments 101 are arranged and a space where an end of the arm 18 is inserted may be disposed. In the space where the filaments 101 are arranged, a plurality of the brushes 102 connected to the end of the arm 18 are inserted. A slit 174 to pull out lead wires 103 connected to the brushes 102 respectively to a space on the opening 171 side is provided along the axial direction of the supporting post 17 on the partition wall 173. Hence, because the space where the filaments 101 are arranged is separated from the opening 171 of the supporting post 17 by the partition wall 173, there is no possibility that an operator comes into contact with the filaments 101 in which large electric power flows. Additionally, the lead wires 103 connected to the brushes 102 can be pulled inside the arm 18 through the slit 174. The arm 18 can be vertically moved on the supporting post 17.

It can be configured to fix the filaments 101 on inner walls as illustrated in FIG. 4 or to arrange the pillar-shaped filaments 101 in a space inside the supporting post 17.

Figure 5:
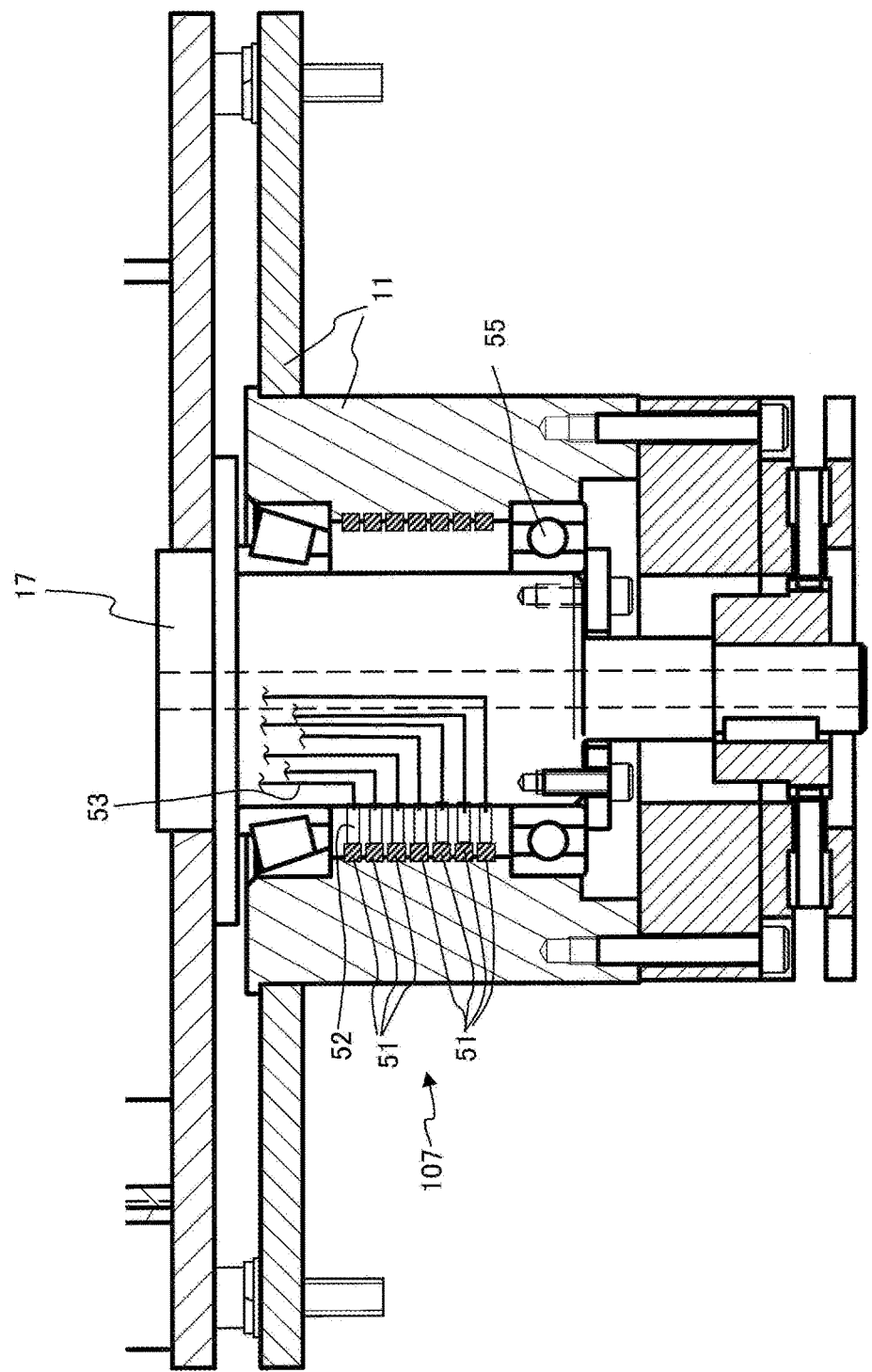
FIG. 5 is a cross-sectional view of a base of the supporting post 17 of the embodiment.

Also, it is desirable that the supporting post 17 can rotate around the axial direction of the supporting post 17 on the carriage 11. In this case, a slip ring 107 is disposed in a contact part between the base of the supporting post 17 and the carriage 11 as illustrated in FIG. 3. The slip ring 107 is configured to include a plurality of conductor rings 51 and a plurality of conductor brushes 52 that come into contact with the rings 51 respectively as illustrated in FIG. 5. Either of a plurality of the rings 51 or the conductor brushes 52 is disposed on the supporting post 17 side and is connected to the filaments 101 electrically. In FIG. 5, as an example, the brushes 52 are arranged on the supporting post 17 side. The brushes 52 are connected to the filaments 101 via the lead wires 53. The other ends (the rings 51 in FIG. 5) are arranged on the carriage 11 side and are connected to the main body 15 electrically.

Figure 7:
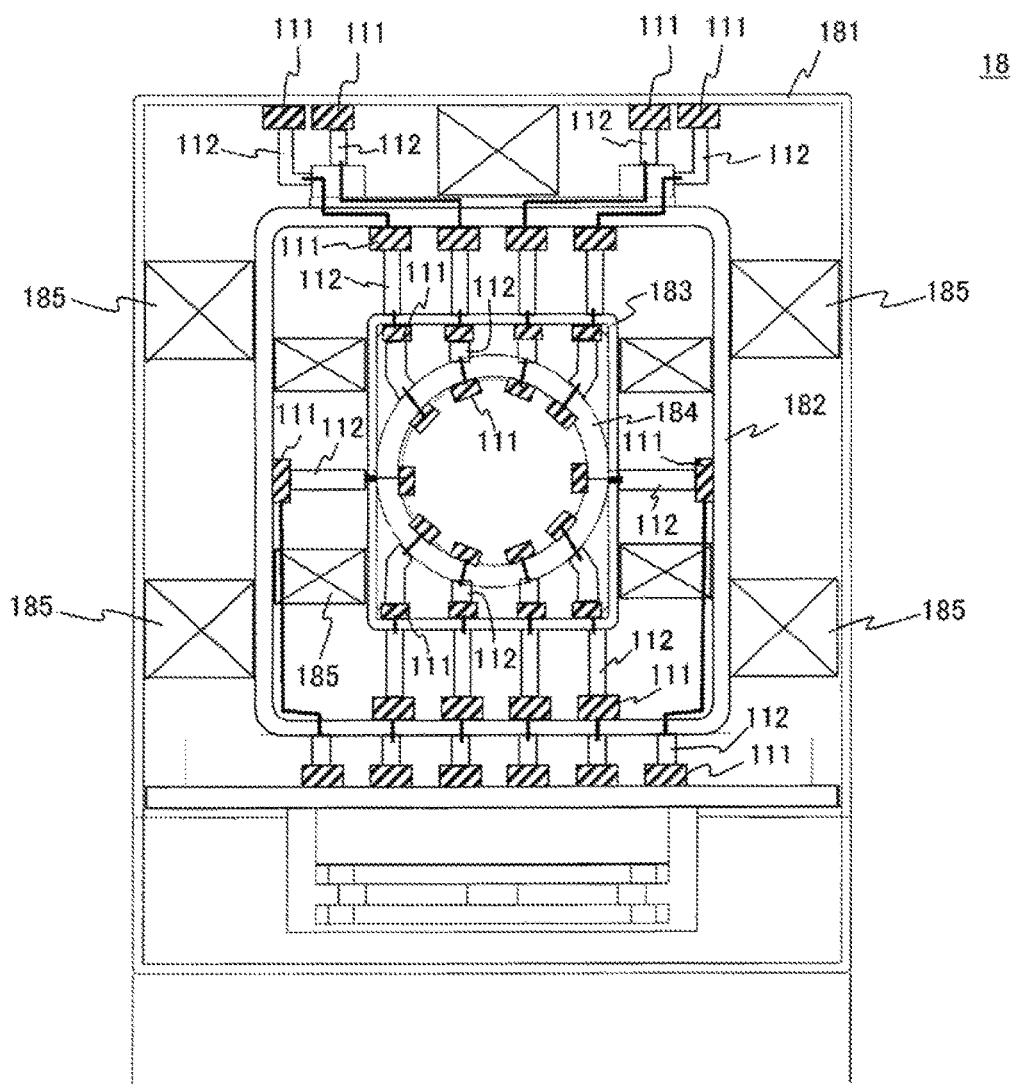
FIG. 7 is a B-B cross-sectional view of the arm 18 of FIG. 3.

Also, as shown in FIG. 7, a plurality of arm filaments 111 electrically connected to a plurality of the arm brushes 112 respectively can be arranged in the arm 18. Hence, electric power can be supplied to the X-ray generator 19 through the arm filaments 111.

Figure 6:
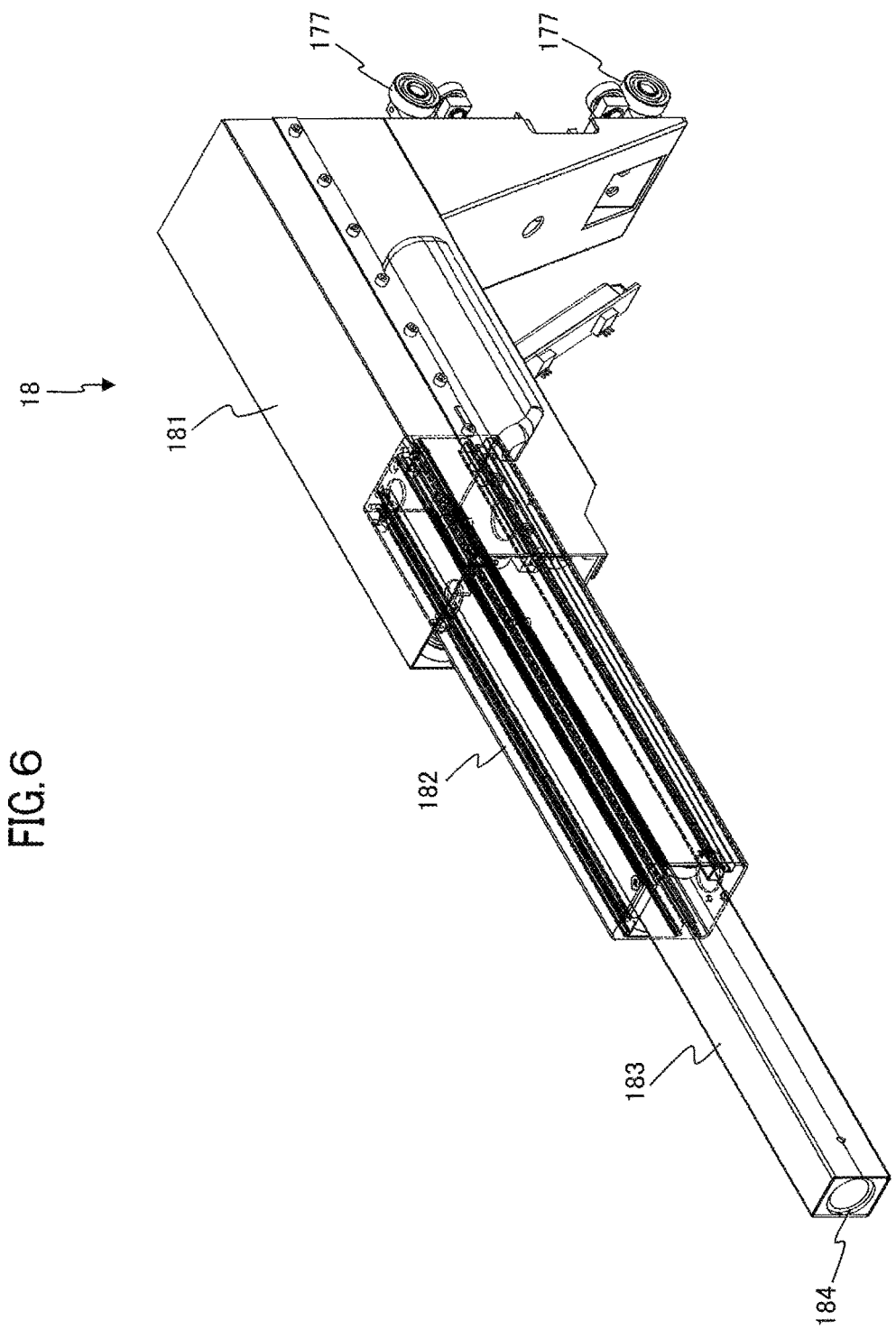
FIG. 6 is a perspective view in a state where an arm of the embodiment is extended.

Also, it is desirable that the arm 18 has an extendable structure. For example, as the perspective view and cross-sectional view are illustrated in FIGS. 6 and 7 respectively, the arm 18 includes a plurality of tubular members 181, 182, 183, and 184 with different thicknesses and has a configuration in which thinner tubular members are inserted in thicker tubular members. Hence, the arm 18 becomes extendable by moving the thinner tubular members in the thicker tubular members in the axial direction. The arm filaments 111 are respectively arranged along the axial direction inside the tubular members 181 and 182. The brushes 112 for the conductor arm are arranged for each of the arm filaments 111 in areas where the thick tubular member 181 and the thin tubular member 182 overlap. Because the arm brushes 112 move along the arm filaments 111 while coming into contact with the arm filaments 111 when the tubular members move in the axial direction, electric power can be supplied to the X-ray generator 19 through the arm filaments 111 and the arm brushes 112 even when the arm 18 is extended.

Figure 8:
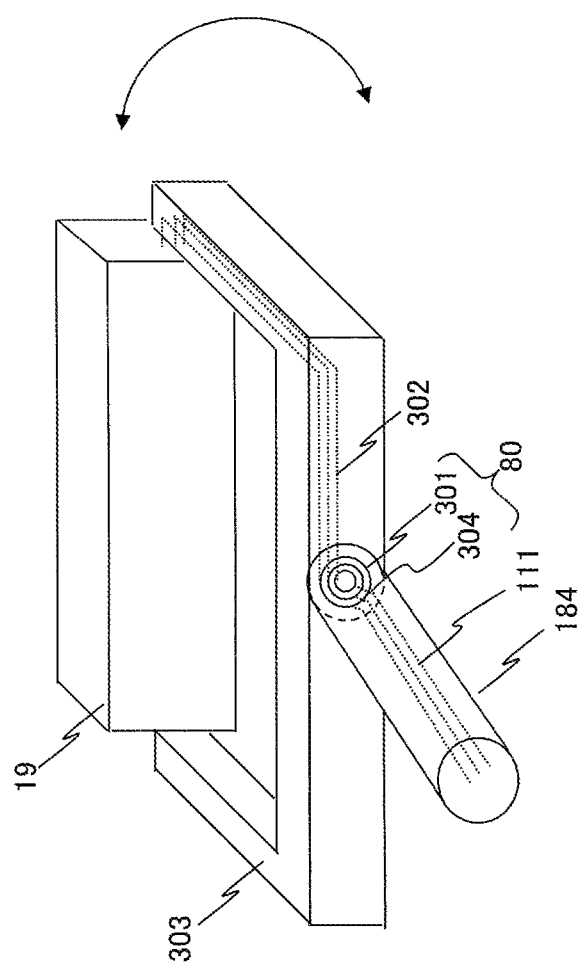
FIG. 8 is an explanatory view that shows a tip of the arm 18 and a connecting part of an X-ray generator 19 of the embodiment.

The X-ray generator 19 is desirably connected to the tip of the arm 18 rotatably around the axial direction of the arm 18. In this case, a slip ring 80 is disposed in a connecting part between the tip of the arm 18 and the X-ray generator 19 as shown in FIG. 8. The arm filaments 111 are electrically connected to any one of a conductor ring 301 and a conductor brush 304 comprising the slip ring 80. In an example of FIG. 8, the arm filaments 111 are connected to the conductor brush 304.

Hereinafter, the details of a specific mobile X-ray imaging apparatus will be described.

The mobile X-ray imaging apparatus of the present invention has a configuration in which the X-ray imaging unit 2 is mounted on the carriage 11 as shown in FIG. 1. The carriage 11 comprises two drive wheels 12 and two front wheels 13, and a driving unit (not illustrated) of the drive wheels 12 and a battery 16 are stored in an inner space of the carriage 11.

Electric power of the battery 16 is used for driving the drive wheels 12.

The X-ray imaging unit 2 is configured by comprising the main body 15, the supporting post 17, the arm 18, the X-ray generator 19, and a collimator 20. The X-ray generator 19 includes the X-ray tube, an anode rotation mechanism that rotates an anode of the X-ray tube, and a detector to detect a tube voltage/a tube current of the X-ray tube respectively.

The collimator 20 includes a movable shield blade for setting an X-ray irradiation field, the driving section, and a light source for irradiating a guide light to the X-ray irradiation field.

The supporting post 17 is mounted at the front of the carriage 11. A bearing 55 and the slip ring 107 are disposed between the base of the supporting post 17 and the carriage 11 as illustrated in FIG. 5.

An X-ray control device 21 and a controller 31 are stored inside the main body 15. The X-ray control device 21 controls electric power (a tube voltage and a tube current) for generating an X-ray to be supplied to the X-ray generator 19 or electric power for rotating an anode of the X-ray tube.

Also, in order to control electric power (a tube voltage and a tube current) to be supplied to the X-ray generator 19, the X-ray control device 21 receives the tube voltage and the tube current detected by the detector of the X-ray generator 19. Therefore, the X-ray control device 21 needs to be connected to the X-ray generator 19 with at least three lead wires (the anode, cathode, and ground wires) for supplying the tube voltage and the tube current to the X-ray generator 19, at least two lead wires for supplying electric power to rotate the anode, and at least four lead wires (two for the tube current and two for the tube voltage) for receiving results of the tube current and the tube voltage detected by the detector, i.e. 10 or more lead wires in total. Here, the X-ray control device 21 and the X-ray generator 19 are connected with the slip ring 107, the filaments 101 of the supporting post 17, the arm filaments 111, the slip ring 80, and the like.

The controller 31 generates a control signal to be transmitted to the X-ray generator 19 for setting an irradiation field of the collimator 20, switching ON and OFF of light irradiation to the irradiation field, and the like. Here, the control signal is transmitted to the collimator 20 by wireless communication.

Also, an operation panel 22 is disposed on the top surface of the main body 15. The operation panel 22 is provided with an operating device for setting X-ray imaging conditions (time products of a tube current and a tube voltage), a press-button switch for X-ray imaging, an operating device for setting an X-ray irradiation field, and the like. Also, on the top surface of the main body 15, provided is a locking mechanism 23 for fixing the arm 18 while the carriage 11 is traveling.

A traveling handle 30 is provided on the main body 15. The traveling handle 30 is provided with a detector (not illustrated) that detects a movement amount added in a back-and-forth direction to the traveling handle 30 by an operator and the direction. The driving unit of the drive wheels 12 drives the drive wheels 12 according to a detection value of the detector.

The supporting post 17 is provided with the opening 171 along the axial direction on the side surface as shown in FIG. 2, and the inner space is separated into three spaces by the partition walls 172 and 173 as shown in FIG. 4.

An end of the arm 18 whose axial direction is horizontal is inserted in a space facing toward the opening 171 as illustrated in FIG. 4. Between the end of the arm 18 and the inner wall of the supporting post 17, a bearing 177 that guides the arm vertically is disposed.

A plurality of the filaments 101 are fixed parallel along the axial direction on the inner wall of a space between the partition walls 172 and 173 inside the supporting post 17. Also, a brush holding part 175 where a plurality of the brushes 102 are mounted is disposed. The brush holding part 175 does not come into contact with the supporting post 17, the partition wall 172, and the partition wall 173 and is connected to the arm 18 with a connecting part 178. The connecting part 178 passes through the slit 174 of the partition wall 173. Therefore, the brush holding part 175 moves vertically with the vertical movement of the arm 18. A plurality of the brushes 102 move vertically while keeping a state where the brushes 102 physically and electrically come into contact with the filaments 101 with the vertical movement of the arm 18.

In a space farthest from the opening 171 of the supporting post 17, the mechanical part (counter-balance mechanism) 40 that allows the arm 18 to manually move along the supporting post 17 vertically is disposed. The mechanical part 40 includes a spring 41 and the like.

The X-ray generator 19 is attached at the tip of the arm 18, and the collimator 20 is attached below the X-ray generator 19. The mechanical part 40 has a structure to apply a force balancing with a total weight of the arm 18, the X-ray generator 19, and the collimator 20. Hence, an operator can vertically move the arm 18 with a small manual force, and the moved position is maintained. Also, an electromagnetic brake 176 for locking a position of the arm 18 is provided on the tip of the arm 18 and the partition wall 173 of the supporting post 17. The electromagnetic brake 176 is operated by the operator's operation and locks the position of the arm 18 with electromagnetic power.

Between the base of the supporting post 17 and the main body, the slip ring 107 is disposed as illustrated in FIG. 5. Although FIG. 5 shows the rings 51 and the brushes 52 of the slip ring 107 by reducing the number of pieces for convenience of illustration, 10 or more pieces of the rings 51 and the brushes 52 are actually provided corresponding to electric power to be transmitted and the detection signal type. A plurality of the brushes 52 of the supporting post 17 are electrically connected to the lower parts of the filaments 101 respectively inside the supporting post 17 with the lead wires 53 (FIG. 5). A plurality of the rings 51 of the slip ring 107 are connected to the X-ray control device 21 with wires that are not illustrated, receive or transmit the electric power to be transmitted and the detection signals.

On the other hand, the arm 18 has a configuration in which the tubular members 181, 182, 183, and 184 with different thicknesses are inserted in order as illustrated in FIGS. 6 and 7. Between the respective tubular members 181 etc., bearings 185 are respectively disposed, and inner tubular members can be smoothly pulled out from and inserted into outer tubular members. Hence, the arm 18 can be extended and contracted. The arm filaments 111, whose number is the same as the arm filaments 101 of the supporting post 17, are respectively fixed on the inner walls of the respective tubular members 181 etc. The arm filaments 111 are attached parallel to the axial direction of the respective tubular members 181 etc. The arm filaments 111 of the outermost tubular member 181 are connected to the arm brushes 102 inserted inside the supporting post 17. Therefore, the arm filaments 111 of the outermost tubular member 181 are electrically connected to the arm filaments 101 of the supporting post 17 through the brushes 102. The inner tubular members 182, 183, and 184 inside the tubular member 181 are respectively provided with the brushes 112 on the outer walls and the arm filaments 111 on the inner walls. Hence, even when the tubular members 181 etc. are extended and contracted, the arm filaments 111 of the outermost tubular member 181 are electrically connected to the arm filaments 111 of the innermost tubular member 184 via the arm filaments 111 of the tubular members 182 and 183 in order.

The tip of the innermost tubular member 184 is connected to the X-ray generator 19 through an X-ray tube supporting mechanism 303 as shown in FIG. 8. The slip ring 80 is disposed in the connecting part between the X-ray tube supporting mechanism 303 and the tubular member 184. Also, the X-ray tube supporting mechanism 303 has a configuration that can rotate around the axis of the innermost tubular member 184. The brush 304 of the slip ring 80 is connected to the tip of the arm filament 111 of the tubular member 184. A ring 301 of the slip ring 80 is disposed on the X-ray generator 19 side and is connected respectively to the X-ray tube (the anode, cathode, and ground wires) of the X-ray generator 19, the anode rotation mechanism, the detector of a tube current and a tube voltage, and the like with the filament or a lead wire 302.

Such a configuration vertically moves the arm 18 on the supporting post 17, and a position of the X-ray generator 19 can be adjusted to an imaging site of an object by extending/contracting the arm 18 and rotating the supporting post 17 on the carriage 11. Then, through the filaments 101 and the arm filaments 111 and the like, electric power and the like are supplied to the X-ray generator 19 by the supporting post 17 and the arm 18 to generate an X-ray, which can execute imaging. Therefore, no cable is provided for the electric power supply, and there is no possibility that a cable comes into contact with an object, which does not generate any problem in infection prevention. Also, an operator can freely adjust a position of the X-ray generator 19 without worrying about cable wiring, which improves the operability.

Also, in the present embodiment, the number of the arm filaments 111 is reduced by transmitting and receiving partial control signals with small electric power using wireless communication, which prevents the supporting post 17 from increase in size.

Specifically, as shown in FIG. 3, it is configured to dispose a transmitter 32 inside the controller 31 of the main body 11 and provide a receiver 33 with the X-ray generator 19 or the collimator 20. Hence, control signals can be transmitted from the controller 31 to the X-ray generator 19 or the collimator 20 by wireless communication between the transmitter 32 and the receiver 33. Because the control signals are often electric signals with small electric power, the control signals can be easily transmitted by wireless communication. By transmitting and receiving the control signals through wireless communication, the number of the filaments 101 to be arranged in the supporting post 17 and the like can be reduced, which can reduce a thickness of the supporting post 17.

For example, control signals can be transmitted and received by wireless communication in order to perform drive control for a shield blade that sets an X-ray irradiation field of the collimator 20 and control ON/OFF of the light source of a guide light in the X-ray irradiation field.

Also, a little electric power is required to operate the receiver 33, and small electric power is also required to drive the shield blade and the light source. Therefore, a battery 105 may be disposed in the X-ray generator 19 or the collimator 20. By supplying electric power from the battery 105 to the receiver 33 and the collimator 20, an X-ray irradiation range of the collimator 20 can be adjusted, and the light can be irradiated to the irradiation range.

Although the battery 105 may be a dry cell battery, a rechargeable battery can be also used. The rechargeable battery 105 can be connected to the main body 15 via the brushes 102 of the arm 18 and the filaments 101 inside the supporting post 17 to charge the electricity while X-ray imaging is not performed. Hence, the filaments exclusive for the battery 105 do not need to be provided, which can reduce the number of the filaments 101.

Figure 9:
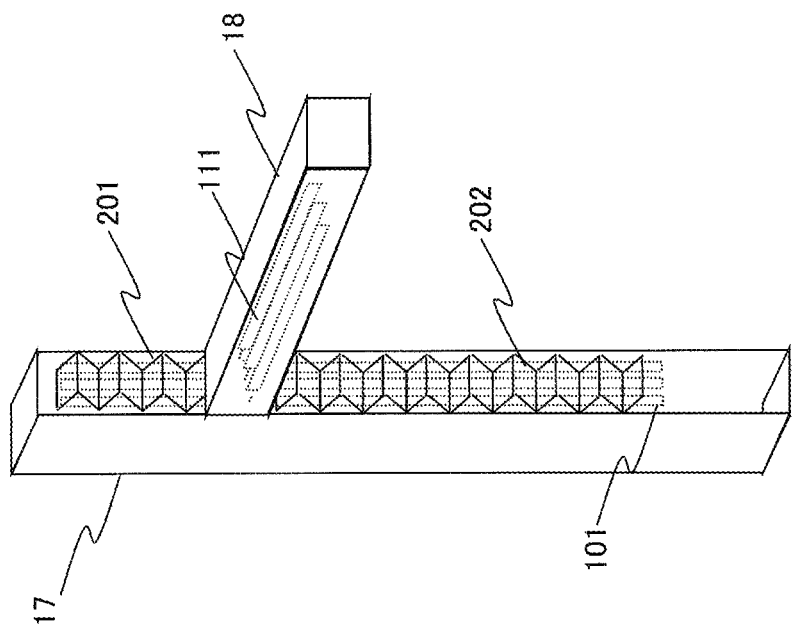
FIG. 9 is a perspective view that shows a shape in which an opening of the supporting post 17 of the embodiment is covered with a bellows.

Although it is configured so that the filaments 101 to which large electric power is supplied are not exposed from the opening 171 of the supporting post 17 by providing the partition wall 173 as illustrated in FIG. 4 in the above embodiment, the insulation bellows 201 and 202 can be also disposed in the opening 171 of the supporting post 17 instead of the partition wall 173 as illustrated in FIG. 9. The bellows 201 and 202 are respectively disposed so as to cover the upper side and the lower side of the opening 171 on the arm 18 as illustrated in FIG. 9. Hence, when the arm 18 is moved to the upper side, the upper bellows 201 contracts, and the lower bellows 202 extends, which maintains a state in which the opening 171 is covered. When the arm 18 is moved to the lower side, the bellows 201 extends, and the bellows 202 contracts. In either case, the filaments 101 can be prevented from being exposed without providing the partition wall 173. An elastic insulation film (for example, a rubber film) can be also used instead of the bellows 201 and 202.

REFERENCE SIGNS LIST

11: carriage
12: drive wheel (rear wheel)
13: front wheel
15: main body
16: battery
17: supporting post
18: arm
19: X-ray generator
20: collimator
21: X-ray control device
22: operation panel
23: locking mechanism
30: traveling handle
31: controller
32: transmitter
33: receiver
40: mechanical part
41: spring
51: rings
52: brushes
53: lead wires
55: bearing
80: slip ring
101: filaments
102: brushes
103: lead wires
105: battery
107: slip ring
111: filaments
112: brushes
172 and 173: partition walls
174: slit
175: brush holding part
176: electromagnetic brake
177: bearing
178: connecting part
181, 182, 183, and 184: tubular members
185: bearings
201 and 202: bellows
301: ring
302: lead wire
303: X-ray tube supporting mechanism
304: brush

The invention claimed is:

1. A mobile X-ray imaging apparatus that has a carriage and an X-ray imaging unit mounted on the carriage,
   wherein the X-ray imaging unit includes an X-ray generator; an arm that holds one end of the X-ray generator; a supporting post that supports the other end of the arm in a vertically movable manner, and a main body that supplies electric power at least to generate an X-ray to the X-ray generator,
   wherein a plurality of conductor filaments are arranged at intervals along an axial direction on the supporting post, a plurality of conductor brushes coming into contact with the filaments respectively are arranged on the other end of the arm, and the brushes move vertically along the filaments in a state of coming into contact with the filaments with vertical movement of the arm, and
   wherein the main body supplies the electric power to the X-ray generator through the filaments and the brushes.

2. The mobile X-ray imaging apparatus according to claim 1,
   wherein an opening is provided along the axial direction on a side surface of the supporting post, and a plurality of the filaments are arranged in a space inside the supporting post, and wherein the other end of the arm is inserted in the opening of the supporting post.

3. The mobile X-ray imaging apparatus according to claim 1,
wherein a plurality of the filaments and a spring to urge the arm in the vertical direction are disposed in a space inside the supporting post, and
wherein the space inside the supporting post is separated into a space in which the filaments are arranged and a space in which the spring is disposed by a partition wall.

4. The mobile X-ray imaging apparatus according to claim 2,
wherein a plurality of the filaments and a mechanical part to hold a desired position in the vertical direction of the arm are disposed in the space inside the supporting post,
wherein first and second partition walls that separates a first space in which the mechanical part is disposed; a second space in which the filaments are arranged; and a third space in which the other end of the arm is inserted are disposed in the supporting post, and
wherein a slit to pull out lead wires connected respectively to a plurality of the brushes arranged in the second space to the third space is provided along the axial direction of the supporting post on the second partition wall separating the second and third spaces.

5. The mobile X-ray imaging apparatus according to claim 1,
wherein the filaments are fixed to an inner wall of the supporting post.

6. The mobile X-ray imaging apparatus according to claim 1,
wherein a base of the supporting post is rotatably supported around the axial direction of the supporting post on the carriage,
wherein a slip ring is disposed in a contact part between the base of the supporting post and the carriage, and the slip ring includes a plurality of conductor rings and a plurality of conductor brushes coming into contact with the rings respectively, and
wherein a plurality of the rings and one ends of a plurality of the conductor brushes are arranged on the supporting post side to electrically connect to the filaments, and the other ends are arranged on the carriage side to electrically connect to the main body.

7. The mobile X-ray imaging apparatus according to claim 1,
wherein a plurality of arm filaments electrically connected to a plurality of the brushes respectively are arranged in the arm, and electric power is supplied to the X-ray generator through the arm filaments.

8. The mobile X-ray imaging apparatus according to claim 7,
wherein the arm includes a plurality of tubular members with different thicknesses, has a configuration in which thinner tubular members are inserted in thicker tubular members, and can be extended/contracted by moving the thinner tubular members to the thicker tubular members in the axial direction, and
wherein the arm filaments are arranged inside the thicker tubular members and thinner tubular members respectively, and brushes for the conductor arm are arranged for each of the arm filaments in areas where the thicker tubular members and thinner tubular members overlap.

9. The mobile X-ray imaging apparatus according to claim 7,
wherein the X-ray generator is connected to the tip of the arm rotatably around the axial direction of the arm, a slip ring is disposed in the connecting part between the tip of the arm and the X-ray generator, and the arm filaments are electrically connected to conductor rings composing the slip ring and one ends of conductor brushes.

10. The mobile X-ray imaging apparatus according to claim 1,
wherein the main body is provided with a controller that generates a control signal to be transmitted to the X-ray generator, the controller and the X-ray generator comprise a transmitter and a receiver respectively, and the control signal is transmitted from the controller to the X-ray generator by wireless communication between the transmitter and the receiver.

11. The mobile X-ray imaging apparatus according to claim 1,
wherein the X-ray generator is provided with a battery that supplies electric power to a collimator that sets an X-ray irradiation range, and
wherein the battery is connected to the main body and is recharged through the brushes on the other end of the arm and the filaments inside the supporting post.

* * * * *